US009979390B2

(12) United States Patent
Fujikawa et al.

(10) Patent No.: US 9,979,390 B2
(45) Date of Patent: May 22, 2018

(54) GRIP SENSOR

(71) Applicant: Panasonic Intellectual Property Management Co., Ltd., Osaka (JP)

(72) Inventors: Shinji Fujikawa, Osaka (JP); Nobuharu Katsuki, Kyoto (JP); Tsuyoshi Nishio, Chiba (JP); Hiroshi Naitou, Osaka (JP); Yuta Okazaki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 407 days.

(21) Appl. No.: 14/691,180

(22) Filed: Apr. 20, 2015

(65) Prior Publication Data

US 2015/0330931 A1 Nov. 19, 2015

(30) Foreign Application Priority Data

May 14, 2014 (JP) .................................. 2014-100088
Jan. 15, 2015 (JP) .................................. 2015-005643

(51) Int. Cl.
*G01R 27/26* (2006.01)
*H03K 17/96* (2006.01)
(Continued)

(52) U.S. Cl.
CPC ............ *H03K 17/9622* (2013.01); *B62D 1/06* (2013.01); *G01N 27/22* (2013.01); *H03K 2217/94026* (2013.01)

(58) Field of Classification Search
CPC ...... H03K 17/9622; H03K 2217/94026; B62D 1/06; G01N 27/22; G01R 27/2605
(Continued)

(56) References Cited

U.S. PATENT DOCUMENTS 7,795,882 B2 * 9/2010 Kirchner .............. H03K 17/962
324/672
8,456,180 B2 * 6/2013 Sitarski ................ H03K 17/955
324/601
(Continued)

FOREIGN PATENT DOCUMENTS

JP 06-027494 A 2/1994
JP 2008-087566 A 4/2008
(Continued)

OTHER PUBLICATIONS

Explanation about the acceleration examination dated Jan. 15, 2015 for the corresponding Japanese Patent Application No. 2015-005643.
(Continued)

*Primary Examiner* — Arleen M Vazquez
*Assistant Examiner* — Steven Yeninas
(74) *Attorney, Agent, or Firm* — Greenblum & Bernstein, P.L.C.

(57) ABSTRACT

A grip sensor includes: a plurality of capacitive detectors which are disposed in a grip of a steering wheel of a vehicle, and output values which vary according to whether a human body is in contact; and a controller which determines, at a preset timing, a reference value to be subtracted from the values output from the plurality of capacitive detectors, to determine whether the human body is in contact, wherein the controller identifies, from among values output from the plurality of capacitive detectors at the preset timing, one or more values each having an absolute value smaller than a first threshold, and determines, as the reference value, one of the one or more values identified or an average of the one or more values identified.

20 Claims, 7 Drawing Sheets

(51) Int. Cl.
  *G01N 27/22* (2006.01)
  *B62D 1/06* (2006.01)
(58) Field of Classification Search
  USPC ........ 74/484 R; 180/271, 272; 324/658–690;
      340/575, 576; 345/173–178; 600/301,
      600/393, 479, 509; 701/36, 41, 43, 14
  See application file for complete search history.

(56) References Cited

U.S. PATENT DOCUMENTS

| | | | | |
|---|---|---|---|---|
| 8,483,913 | B2* | 7/2013 | Hsu | B62D 5/0457 |
| | | | | 701/41 |
| 9,114,825 | B2 | 8/2015 | Nishijima | |
| 9,287,864 | B2* | 3/2016 | Buttolo | H03K 17/955 |
| 2010/0121530 | A1* | 5/2010 | Suzuki | B62D 5/0457 |
| | | | | 701/41 |
| 2011/0125002 | A1* | 5/2011 | Ershov | A61B 5/0428 |
| | | | | 600/384 |
| 2012/0116239 | A1* | 5/2012 | Kato | A61B 5/0408 |
| | | | | 600/509 |
| 2012/0212240 | A1* | 8/2012 | Young | G01R 27/2605 |
| | | | | 324/679 |
| 2013/0239733 | A1 | 9/2013 | Nishijima | |
| 2015/0049057 | A1* | 2/2015 | Citta | G06F 3/044 |
| | | | | 345/174 |
| 2015/0159419 | A1* | 6/2015 | Van Wiemeersch | E05F 15/77 |
| | | | | 701/36 |
| 2015/0254955 | A1* | 9/2015 | Fields | G08B 21/02 |
| | | | | 705/4 |

FOREIGN PATENT DOCUMENTS

| | | |
|---|---|---|
| JP | 2010-023699 A | 2/2010 |
| JP | 4676408 B | 4/2011 |
| JP | 2013-193475 A | 9/2013 |
| JP | 2014-075219 A | 4/2014 |

OTHER PUBLICATIONS

Japanese Office Action issued in corresponding Japanese Patent Application No. 2015-005643, dated Feb. 24, 2015.

* cited by examiner

GRIP SENSOR

CROSS REFERENCE TO RELATED APPLICATIONS

The present application is based on and claims priority of Japanese Patent Application No. 2014-100088 filed on May 14, 2014 and Japanese Patent Application No. 2015-005643 filed on Jan. 15, 2015. The entire disclosures of the above-identified applications, including the specifications, drawings and claims are incorporated herein by reference in their entirety.

BACKGROUND OF THE INVENTION

1. Field of the Invention

The present disclosure relates to a grip sensor for a steering wheel, which detects contact of a human body, based on a change in capacitance.

2. Description of the Related Art

For example, Patent Literature (PTL) 1 has proposed a conventional information input device which includes a grip sensor that detects contact of a human body, based on a change in capacitance.

According to PTL 1, the curved surface of a grip of a steering wheel includes, on the right and left when viewed from a driver, information input interfaces which receive information from the driver. The information input interfaces each include, for example, electrode groups in exclusive areas and an electrode group in an input area. These electrode groups are disposed being insulated from other electrode groups. If the driver's hand touches one of the electrode groups, the electrode groups can independently measure an amount of change in capacitance. The information input device can detect contact of the driver's hand, based on the measured amounts of change in capacitance.

CITATION LIST

Patent Literature

PTL 1: Japanese Patent No. 4,676,408

SUMMARY OF THE INVENTION

A grip sensor according to the present disclosure includes a plurality of capacitive detectors which are disposed in a grip of a steering wheel of a vehicle, and output values which vary according to whether a human body is in contact. In addition, the grip sensor includes a controller which determines, at a preset timing, a reference value to be subtracted from the values output from the plurality of capacitive detectors, to determine whether the human body is in contact. The controller identifies, from among values output from the plurality of capacitive detectors at the preset timing, one or more values each having an absolute value smaller than a first threshold, and determines, as the reference value, one of the one or more values identified or an average of the one or more values identified.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DETAILED DESCRIPTION OF THE PREFERRED EMBODIMENTS

A description is given of a problem of a conventional configuration, prior to exemplary embodiments of the present disclosure. The above conventional information input device needs to store a value measured when a hand is not in contact as a reference value and subtract the reference value from a measured value, in order to measure an amount of change in capacitance due to contact of a human body with a grip. However, for example, when the information input device is started while a hand is in contact with the left information input interface, a value measured while the hand is in contact is determined as an initial reference value. In this case, the initial reference value includes an error, and thus the amount of change in capacitance cannot be measured properly. The following describes a configuration for addressing such a problem.

It should be noted that an exemplary embodiment and variations described below each show a preferable, specific example. The numerical values, shapes, materials, constituent elements, the arrangement and connection of the constituent elements, steps, the processing order of the steps, and the like described in the following embodiment and variations are mere examples, and thus are not intended to limit the present disclosure. The present disclosure is defined by the scope of the claims. Thus, although a constituent element which is included in the constituent elements in the embodiment and variations below and is not described in independent claims each showing the broadest concept of the present disclosure is not necessarily needed in order to achieve the object of the present disclosure, such a constituent element will be described for a description of a more preferred configuration.

Exemplary Embodiment

Figure 1:
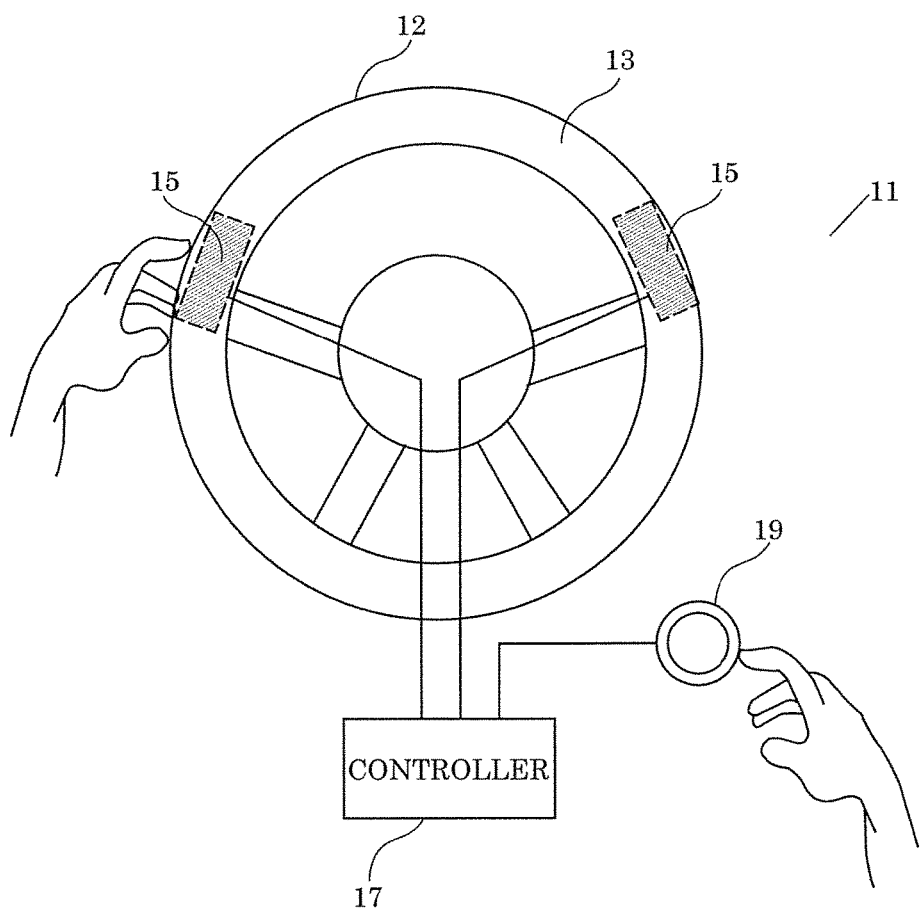
FIG. 1 illustrates a schematic structure of a grip sensor according to an exemplary embodiment of the present disclosure.
Figure 2:
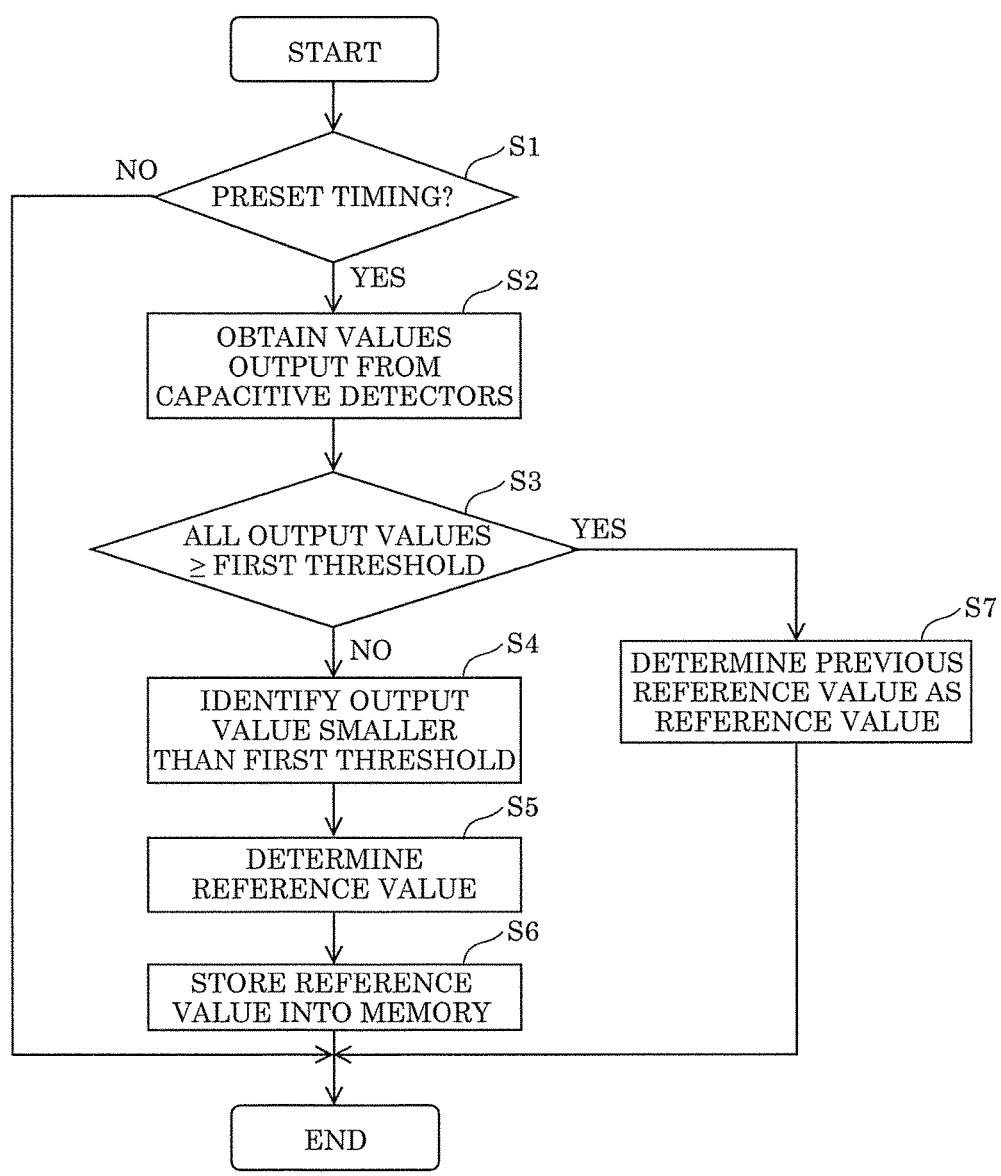
FIG. 2 is a flowchart showing processing by a controller of the grip sensor according to the exemplary embodiment of the present disclosure.
Figure 3:
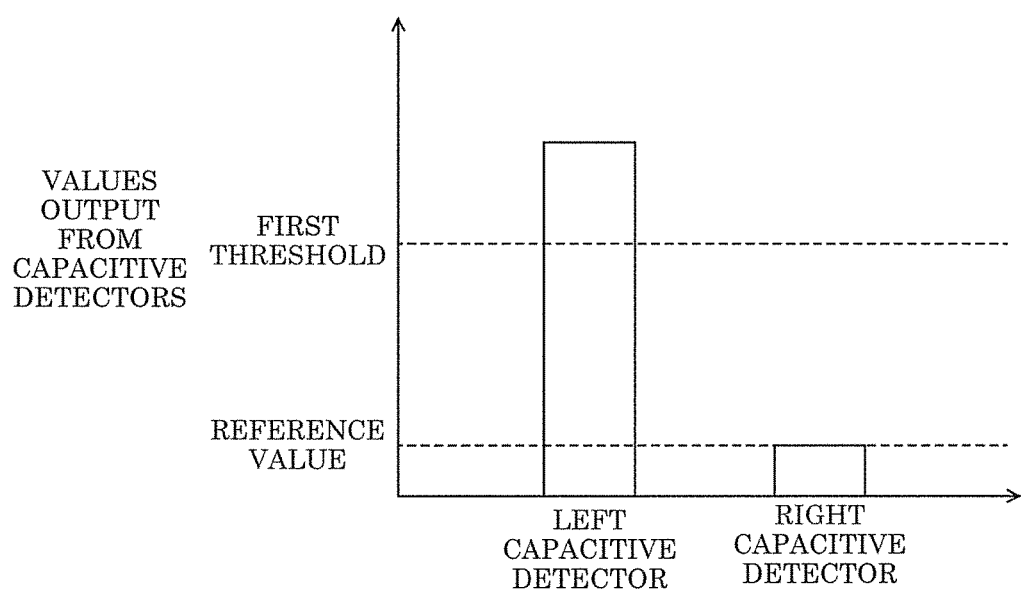
FIG. 3 illustrates sensor output values when a reference value for the grip sensor is determined, according to the exemplary embodiment of the present disclosure.

FIG. 1 illustrates a schematic structure of a grip sensor according to an exemplary embodiment, FIG. 2 is a flowchart showing processing, and FIG. 3 illustrates values output when a reference value for the grip sensor is determined.

In FIG. 1, grip sensor 11 includes a plurality of capacitive detectors 15 which output values which vary according to whether a human body is in contact. Capacitive detectors 15 are disposed in grip 13 of steering wheel 12 of a vehicle. Furthermore, grip sensor 11 includes controller 17 which determines, at a preset timing, a reference value to be subtracted from values output from capacitive detectors 15, to determine whether the human body is in contact. Controller 17 identifies, from among values output from capacitive detectors 15 at the preset timing, one or more values each having an absolute value smaller than a preset threshold, and determines, as the reference value, one of the one or more values identified or an average of the one or more values identified.

Accordingly, a reference value is determined using values output from capacitive detectors 15 at the preset timing, excluding an output value having an absolute value greater than or equal to the preset threshold. In this manner, even if a hand is in contact with grips 13 at a portion in which one of capacitive detectors 15 is disposed, a value output from the one of capacitive detectors 15 is not used for the determination of the reference value. Consequently, this achieves a reduction in a possibility that the reference value for capacitive detectors 15 includes an error.

The following describes in detail the configuration and operation according to the present exemplary embodiment.

As illustrated in FIG. 1, grip sensor 11 includes a plurality of capacitive detectors 15 (two on the right and left in the present exemplary embodiment) which are disposed in grip 13 of steering wheel 12 provided in a vehicle. Capacitive detectors 15 each include an electrode pattern and are formed under the surface of grip 13. Thus, the driver's hand does not directly touch the electrode patterns. The electrode patterns of capacitive detectors 15 are insulated from another electrode pattern. If a driver holds grip 13, a capacitance value changes between the palm of the driver's hand and the electrode patterns. Two capacitive detectors 15 on the right and left are adjusted so as to output the same values in a state where a hand is not in contact with grip 13, when steering wheel 12 is manufactured. It should be noted that although the configuration includes two capacitive detectors 15, the configuration is not limited to this, and it is sufficient if two or more capacitive detectors 15 are included.

In addition, if steering wheel 12 includes a steering heater, capacitive detectors 15 may also serve as heater wires of the steering heater (not illustrated). In this case, the inner structure of grip 13 in a vehicle having heater wires is simplified.

Capacitive detectors 15 are electrically connected to controller 17 which includes a microcomputer, for instance. Accordingly, the output from capacitive detectors 15 is captured by controller 17.

Ignition switch 19 of the vehicle is also electrically connected to controller 17, and a reference value for grip sensor 11 is initialized based on a signal from ignition switch 19. The initialization at this preset timing causes controller 17 to determine a reference value for capacitive detectors 15. The determined reference value is stored in a memory (not illustrated).

Here, the reference value for capacitive detectors 15 is equivalent to a value output from each capacitive detector 15 when a human body makes substantially no approach or contact. Even if a human body makes substantially no approach or contact, values output from capacitive detectors 15 may vary over time due to the vehicle being used, for instance. Accordingly, at every preset timing, controller 17 measures values output from capacitive detectors 15 to initialize and update the reference value. Then, controller 17 determines whether the driver is holding grip 13, from differences between the reference value and values output from capacitive detectors 15.

In the above case, the preset timing is a time when operation of ignition switch 19 of the vehicle is detected. It should be noted that the preset timing (here, when the vehicle is started) is not limited to the time when operation of ignition switch 19 is detected. Examples of the preset timing include times when the following, for instance, are detected: a door being unlocked when the vehicle is to be used; the door being opened; a driver being seated in a driver seat; and the driver wearing a seat belt.

However, when the door is unlocked or opened, the vehicle is still parked, and the driver has not got into the vehicle yet. Accordingly, if power is consumed only to initialize a reference value for grip sensor 11, that power is wastefully consumed. In view of this, as in the present exemplary embodiment, a reference value for grip sensor 11 is initialized when operation of ignition switch 19 of a vehicle is detected, for example.

Next is a description of the operation by such grip sensor 11, with reference to the flowchart in FIG. 2. It should be noted that the following gives a description assuming that values output from capacitive detectors 15 have a positive sensitivity. Thus, if a driver holds grip 13 at a portion in which capacitive detector 15 is disposed, the value output from capacitive detector 15 increases due to a change in capacitance.

First, controller 17 detects whether a time is a preset timing (step S1). For example, if a driver gets in a vehicle and operates ignition switch 19, power is supplied to controller 17 so that controller 17 is activated. If controller 17 detects this preset timing (Yes in step S1), controller 17 performs initialization processing for determining a reference value for right and left capacitive detectors 15. Here, if the time is not a preset timing (No in step S1), processing ends without performing this initialization processing.

As illustrated in FIG. 1, suppose that ignition switch 19 is operated by one hand while a driver holds, with the other hand, grip 13 at a portion in which left capacitive detector 15 is disposed. The values output from right and left capacitive detectors 15 at that time are different, as illustrated in FIG. 3. Thus, a value output from capacitive detector 15 held by the driver is greater than the value output from capacitive detector 15 not held. If the greater one of the output values is determined as a reference value for left capacitive detector 15, this value has a great error relative to an original reference value (a value output from right capacitive detector 15 to/with which a human body makes substantially no approach or contact).

In view of this, controller 17 performs initialization processing for determining a reference value for capacitive detectors 15 as follows. First, controller 17 obtains values output from right and left capacitive detectors 15 (step S2). Then, controller 17 compares the values output from capacitive detectors 15 with a preset threshold (step S3).

Here, a preset threshold is a value for controller 17 to determine that an output value greater than or equal to the preset threshold cannot be used as a reference value (hereinafter, the preset threshold is referred to as a first threshold). If a value output from capacitive detector 15 is greater than or equal to the first threshold, it is assumed that a human body is close to or is in contact with grip 13 at a portion in which capacitive detector 15 is disposed. This first threshold is determined in advance and stored in the memory (not illustrated).

Next, in step S3, if at least one of the values output from right and left capacitive detectors 15 is smaller than the first threshold (No in step S3), controller 17 identifies an output value smaller than the first threshold (step S4). For example, in the case illustrated in FIG. 3, controller 17 identifies a value output from right capacitive detector 15 (step S4). Then, controller 17 determines this output value as a reference value since controller 17 has identified only this value output from right capacitive detector 15 (step S5). Subsequently, controller 17 causes the memory (not illustrated) to store the determined reference value (step S6).

If processing of step S3 shows that values output from both right and left capacitive detectors 15 are smaller than the first threshold (No in step S3), controller 17 identifies the values output from right and left capacitive detectors 15 (step S4). In this case, controller 17 determines one of the values output from right and left capacitive detectors 15 as a reference value by processing of step S5. For example, controller 17 determines a smaller one of the values output from right and left capacitive detectors 15, as a reference value. Alternatively, controller 17 determines an average of the values output from right and left capacitive detectors 15 as a reference value. Determining a reference value in the above manner decreases the error of grip sensor 11.

It should be noted that if a driver holds, with both hands, grip 13 at portions in which right and left capacitive detectors 15 are disposed, the driver cannot operate ignition switch 19. Accordingly, if the driver holds, with one hand, grip 13 at a portion in which capacitive detector 15 is disposed, at least one of right and left capacitive detectors 15 outputs a greater value than the other detector. In addition, if both hands of the driver are not on the portions of grip 13 in which right and left capacitive detectors 15 are disposed, right and left capacitive detectors 15 output small values. Accordingly, controller 17 can determine a reference value, independently of where the driver's hands are.

In addition, although a description has been given of a configuration which includes two capacitive detectors 15 on the right and left, three or more capacitive detectors may be disposed. For example, if the configuration includes four capacitive detectors 15 in the upper, lower, right and left portions of grip 13, suppose that a driver operates ignition switch 19 with the right hand while holding, with the left hand, grip 13 at the portion in which left capacitive detector 15 is disposed. In this case, only the value output from left capacitive detector 15 is greater than the first threshold. Thus, controller 17 identifies values output from three capacitive detectors 15 other than left capacitive detector 15, through the processing of step S4. Controller 17 determines a reference value for capacitive detectors 15, based on the values output from three capacitive detectors 15 other than left capacitive detector 15 (step S5). In this case, values output from three capacitive detectors 15, namely values except for the greatest value output from left capacitive detector 15, are substantially the same, and thus controller 17 determines one of the output values as a reference value, for example. Controller 17 may determine the smallest output value as a reference value. Alternatively, controller 17 may determine an average of values output from three capacitive detectors 15 as a reference value. If an average is used, an error of a reference value is further reduced. Determining the reference value in the above manner decreases the error in detection by grip sensor 11.

Figure 4:
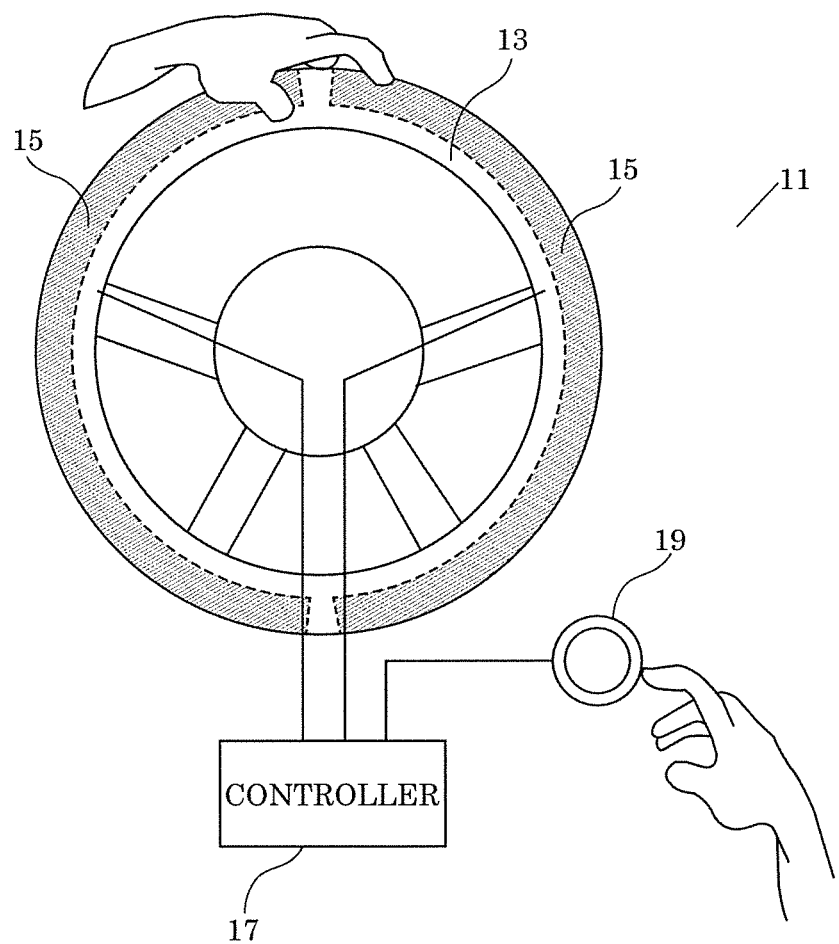
FIG. 4 illustrates a schematic structure of the grip sensor according to the exemplary embodiment of the present disclosure.
Figure 5:
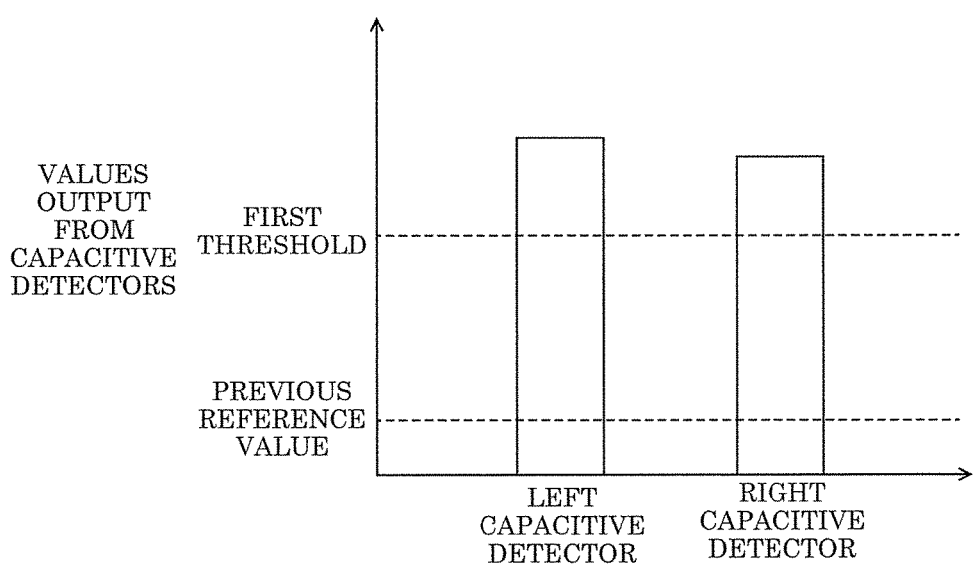
FIG. 5 illustrates sensor output values when a reference value for the grip sensor is determined, according to the exemplary embodiment of the present disclosure.

Next is a description of processing in step S3 of the flowchart shown in FIG. 2 performed when both the values output from right and left capacitive detectors 15 are greater than or equal to the first threshold (Yes in step S3). If both the values output from right and left capacitive detectors 15 are greater than or equal to the first threshold, controller 17 determines, as a reference value, a reference value previously determined (hereinafter, referred to as a previous reference value), which is currently stored in the memory (not illustrated), rather than updating the reference value (step S7). The following describes a specific example in this case, with reference to FIGS. 4 and 5. FIG. 4 illustrates a schematic structure of grip sensor 11, and FIG. 5 illustrates values output when a reference value for grip sensor 11 is determined.

FIG. 4 illustrates a configuration in which right and left capacitive detectors 15 are each disposed substantially half along grip 13. In this manner, it is possible to detect hold of grip 13 by a driver even if the driver holds anywhere of grip 13. For example, suppose that the driver operates ignition switch 19 while the left hand is put on grip 13 at a portion over right and left capacitive detectors 15 since capacitive detectors 15 are long, as illustrated in FIG. 4. In this case, the palm of the driver's hand is on both capacitive detectors 15, and thus values output from both the detectors are high and greater than the first threshold, as illustrated in FIG. 5. Accordingly, if a reference value is determined based on one of the output values, the reference value will be a value greater than a reference value obtained when a hand is not in contact with grip 13, which results in a great error.

Thus, controller 17 determines a previous reference value as a current reference value for all capacitive detectors 15 (step S7). Accordingly, controller 17 ends initialization processing while keeping the previous reference value without changing the reference value stored in the memory (not illustrated). Determining a reference value in the above manner prevents a great error in detection by grip sensor 11.

The above configuration and operation allow controller 17 to identify, from among values output from capacitive detectors 15 at a preset timing, one or more values smaller than the first threshold, and determine, as the reference value, one of the one or more values identified or an average of the one or more values identified. Accordingly, even if a hand is in contact with grip 13 at a portion in which one of capacitive detectors 15 is disposed, a value output from the one of capacitive detectors 15 is not used as the reference value. Consequently, this achieves a reduction in a possibility that the reference value for grip sensor 11 includes an error.

It should be noted that although the above description is given assuming that capacitive detectors 15 have a positive sensitivity, capacitive detectors 15 may have a negative sensitivity depending on the circuit configuration. In this case, a value output from capacitive detector 15 at a portion not held by a driver is greater than a value output from capacitive detector 15 at a portion held by the driver. Thus, controller 17 identifies, from among values output from capacitive detectors 15 at a preset timing, one or more values greater than the first threshold, and determines, as the reference value, one of the one or more values identified or an average of the one or more values identified. Such a configuration achieves equivalent effects as those achieved when capacitive detectors 15 have a positive sensitivity.

Processing of determining a reference value by controller 17 when capacitive detectors 15 have a positive sensitivity and when capacitive detectors 15 have a negative sensitivity can be put into one expression below. Specifically, processing of steps S3 to S5 can be expressed as follows: controller 17 identifies, from among values output from capacitive detectors 15 at a preset timing, one or more values each having an absolute value smaller than the first threshold, and determines, as the reference value, one of the one or more values identified or an average of the one or more values identified. Similarly, processing of steps S3 and S7 can be expressed as follows: controller 17 determines a previous reference value as the reference value if all the values output from capacitive detectors 15 at the preset timing have absolute values greater than or equal to the first threshold.

Although the preset timing is a time when ignition switch 19 is operated in the present exemplary embodiment, the preset timing is not limited to this. The preset timing may be at least one of times when the following are detected: operation of a shift lever; operation of a switch on an instrument panel of a driver seat; and operation of a switch of a driver door. In such cases, a driver is the one who operates a shift lever and a switch, and thus either right or left hand of the driver must be away from grip 13 when the driver operates the shift lever or the switch. Even if values output from capacitive detectors 15 in a state where a human body makes substantially no approach or contact vary over time due to the vehicle being used, the reference value is corrected at such timings, and thus the error of grip sensor 11 further decreases. It should be noted that the error of grip sensor 11 is further reduced if the preset timing is set to all the times when the following are detected: operation of ignition switch 19 of the vehicle; operation of a shift lever; operation of a switch on an instrument panel of a driver seat; and operation of a switch of a driver door.

In addition, if the configuration includes three or more capacitive detectors 15, a possibility is low that a driver holds grip 13 at all the portions in which capacitive detectors 15 are disposed. Even if the driver holds any two of capacitive detectors 15 with both hands, capacitive detector 15 which is not held is present. Thus, in the case of this configuration, a reference value for all capacitive detectors 15 may be corrected at preset time intervals (one-minute intervals, for example), based on a value output from capacitive detector 15 which is not held. In this case, the preset timing corresponds to a time when a preset time period elapses. Even if values output from capacitive detectors 15 in a state where a human body makes substantially no approach or contact vary over time due to the vehicle being used, the reference value is corrected at preset time intervals, and thus the error of grip sensor 11 is further reduced.

First Variation

Figure 6:
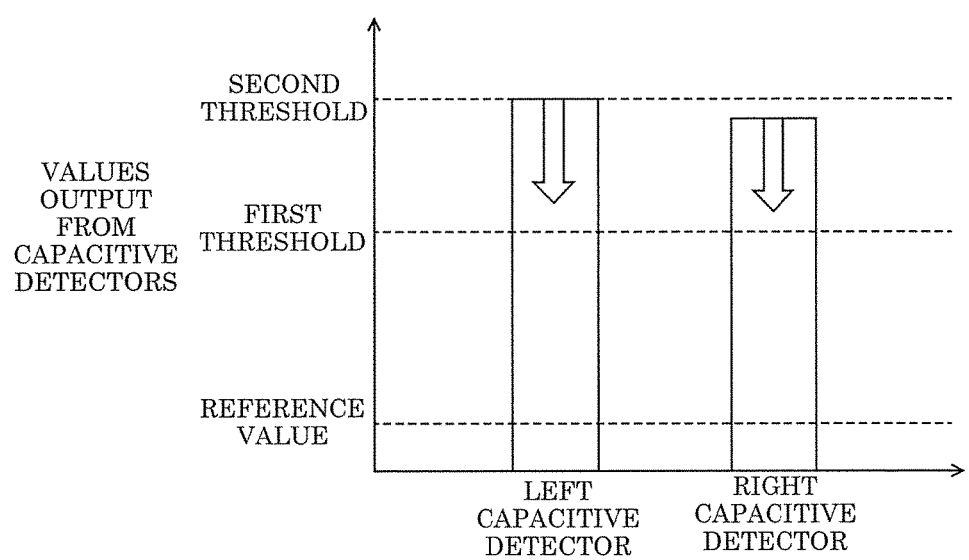
FIG. 6 illustrates sensor output values when a sensitivity of the grip sensor is adjusted according to a first variation of the exemplary embodiment of the present disclosure.

FIG. 6 illustrates sensor output values when a sensitivity of grip sensor 11 is adjusted. If an output value has reached a second threshold which is greater than the first threshold when grip sensor 11 has a positive sensitivity, controller 17 adjusts a sensitivity to the extent that the output value is below the second threshold, based on the magnitude of the output value. In addition, if an output value is below a second threshold which is smaller than the first threshold when grip sensor 11 has a negative sensitivity, controller 17 adjusts a sensitivity to the extent that the output value does not fall below the second threshold, based on the magnitude of the output value. This second threshold is a value set in order to determine whether capacitive detector 15 has trouble. Specifically, if a positive output value has reached the second threshold, capacitive detector 15 is determined to have trouble. However, if an output value has reached the second threshold due to the driver's large hand when capacitive detector 15 has a positive sensitivity, grip sensor 11 may be determined to have trouble even though grip sensor 11 has no trouble. In view of this, in the present exemplary embodiment, the sensitivity of capacitive detector 15 is lowered if an output value has reached the second threshold, thus preventing incorrectly determining that grip sensor 11 has trouble. Specifically, in the present exemplary embodiment, controller 17 determines that capacitive detector 15 does not have trouble if a value output from capacitive detector 15 stably approaches zero by lowering the sensitivity of capacitive detector 15. If the output value does not approach zero, controller 17 determines that capacitive detector 15 has trouble.

The following describes in detail a first variation of the above exemplary embodiment. Here, the definition of the first threshold is the same as that in the above exemplary embodiment. It should be noted that capacitive detectors 15 have a positive sensitivity. In addition, the reference value is determined based on the operation according to the above exemplary embodiment. In FIG. 6, although values output from right and left capacitive detectors 15 are substantially the same, but with a slight difference, the value output from left capacitive detector 15 has reached the second threshold. Here, the second threshold is an invariable maximum value output from capacitive detector 15 having trouble (a minimum output value if capacitive detector 15 has a negative sensitivity). The second threshold is stored in advance in a memory (not illustrated). Thus, controller 17 determines that capacitive detector 15 has trouble if a value output therefrom reaches the second threshold.

The large driver's hand may cause capacitive detector 15 to output a great value reaching the second threshold. In that case, controller 17 incorrectly determines that left capacitive detector 15 has trouble. In view of this, controller 17 makes adjustment to lower a sensitivity of capacitive detector 15 which has output a value reaching the second threshold. Specifically, controller 17 adjusts a sensitivity so that a value output from capacitive detector 15 is at least the first threshold and smaller than the second threshold. For example, controller 17 makes adjustment to lower sensitivities by the amounts indicated by the arrows. At this time, if a value output from left capacitive detector 15 decreases as well by lowering the sensitivity, this shows that left capacitive detector 15 is normally operating, and the cause of the output value reaching the second threshold is the driver's large hand. If the output value does not change, controller 17 determines that left capacitive detector 15 has trouble. Such an operation decreases the possibility of incorrect determination and reduces the error of grip sensor 11.

It should be noted that if the driver's hand is small, an output value is small, on the contrary. Accordingly, if a value output from capacitive detector 15 is small, a sensitivity may be increased to the extent that the output value does not reach the second threshold. In this case, the sensitivity increases, thus improving the accuracy of detection and reducing the error.

According to the above operation, if one of the values output from capacitive detectors 15 at a preset timing reaches the second threshold, controller 17 adjusts a sensitivity based on the magnitude of the output value. Thus, incorrect determination of trouble can be prevented, and the error of grip sensor 11 is reduced.

It should be noted that capacitive detectors 15 having a negative sensitivity may be used. In this case, if a value output from capacitive detector 15 reaches the second threshold, controller 17 makes adjustment to lower the sensitivity of capacitive detector 15 which has output the value, based on the magnitude of the output value. If the driver's hand is small, controller 17 increases a sensitivity to the extent that the output value does not fall below the second threshold. This reduces the error of detection by grip sensor 11.

Processing of adjusting a sensitivity by controller 17 when capacitive detectors 15 have a positive sensitivity and when capacitive detectors 15 have a negative sensitivity described above can be put into one expression below. Specifically, the processing can be expressed as follows: if the values output from capacitive detectors 15 at the preset timing include a value having an absolute value greater than or equal to a second threshold which is greater than the first threshold, controller 17 adjusts, based on magnitude of the value, a sensitivity of one of capacitive detectors 15 which has output the value to the extent that the value is below the second threshold.

Second Variation

Figure 7:
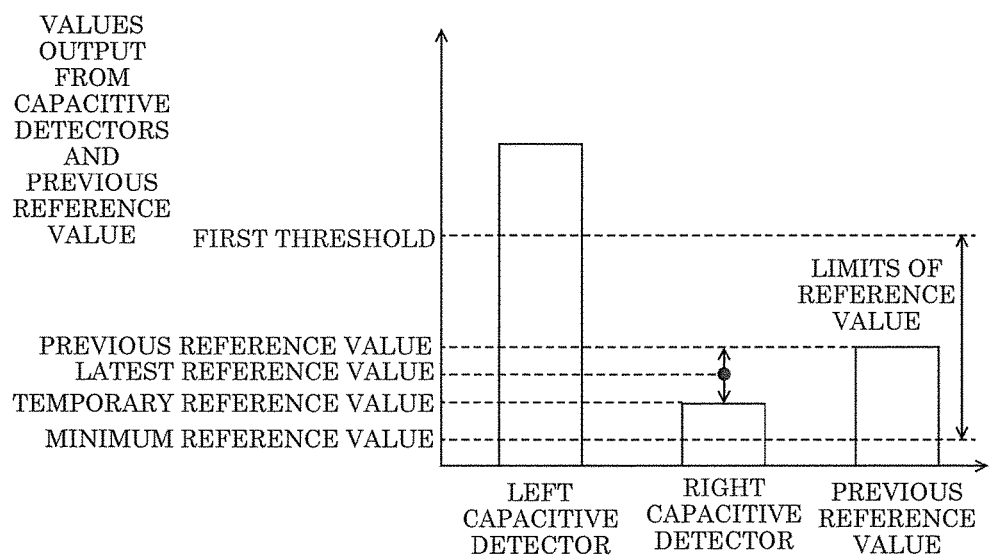
FIG. 7 illustrates sensor output values when a reference value for the grip sensor is determined according to a second variation of the exemplary embodiment of the present disclosure.

FIG. 7 illustrates sensor output values when a reference value for grip sensor 11 is determined according to a second variation of the above exemplary embodiment. A minimum reference value smaller than the first threshold is set for a reference value when grip sensor 11 has a positive sensitivity. Controller 17 re-determines a reference value if a determined reference value is between the first threshold and the minimum reference value smaller than the first threshold, based on a previous reference value and the determined reference value. In addition, a minimum reference value having an absolute value smaller than the first threshold is set for a reference value when grip sensor 11 has a negative sensitivity. If the determined reference value is between the first threshold and the minimum reference value, controller 17 re-determines a reference value based on a previous reference value and the determined reference value. In this manner, a past reference value gives influence onto the next reference value, and thus a reference value for grip sensor 11 less varies.

The following describes in details the second variation of the above exemplary embodiment. It should be noted that the definition of the first threshold is the same as that in the above exemplary embodiment. Capacitive detectors 15 have a positive sensitivity.

FIG. 7 illustrates values output from right and left capacitive detectors 15 when ignition switch 19 is operated in a state where the left hand is in contact with grip 13 at a portion in which capacitive detector 15 is disposed. The "left capacitive detector" and the "right capacitive detector" in FIG. 7 are the same as those in FIG. 3 described in the above exemplary embodiment. Controller 17 once determines a value output from right capacitive detector 15 as a reference value, and thereafter determines a latest reference value in consideration of the previous reference value. Specifically, controller 17 averages a previous reference value and a temporary reference value determined this time (hereinafter, referred to as a temporary reference value), to re-determine a latest reference value (black dot in FIG. 6). Repeating this processing keeps giving, the previous reference value, influence of the reference values used by then, and thus the obtained latest reference value is less influenced by, for instance, noise which causes variations in the reference value.

It should be noted that the minimum reference value is a value used by controller 17 to determine that capacitive detector 15 has trouble such as disconnection, if a value output from capacitive detector 15 is smaller than the minimum reference value. The minimum reference value is stored in advance in a memory (not illustrated). Accordingly, if an output value is smaller than the minimum reference value for trouble determination, controller 17 does not use the output value and informs a driver of trouble by warning light or an alarm, and then stops operation of grip sensor 11.

Controller 17 identifies one or more output values smaller than the first threshold from among values output from capacitive detectors 15 at a preset timing, and determines, as a temporary reference value, one of the one or more output values identified or an average of the one or more output values identified. For example, controller 17 determines a value output from right capacitive detector 15 as a temporary reference value, in FIG. 7. Controller 17 calculates a latest reference value by averaging the temporary reference value and the previous reference value, as described above, if the temporary reference value is in the limits of a reference value. Here, the limits of a reference value indicate a range between the minimum reference value and the first threshold as illustrated in FIG. 7.

It should be noted that other than the method of re-determining the latest reference value by averaging the previous reference value and a temporary reference value as described above, the latest reference value may be re-determined with a statistical technique such as obtaining a weighted average.

The above operation allows a past reference value to give influence onto the next reference value, and thus a reference value for grip sensor 11 less varies.

It should be noted that capacitive detector 15 may have a negative sensitivity. In this case, if the determined reference value is between the first threshold and the minimum reference value having an absolute value smaller than the first threshold, controller 17 re-determines a reference value, based on a previous reference value and the determined reference value. This also achieves equivalent effects as those obtained when capacitive detector 15 has a positive sensitivity.

In addition, also in the first and second variations of the above exemplary embodiment, the preset timing may include at least one of times when the following are detected: operation of ignition switch 19 of a vehicle; operation of a shift lever; operation of a switch on an instrument panel of a driver seat; operation of a switch of a driver door; a driver being seated in the driver seat; and the driver wearing a seat belt.

It should be noted that although the present disclosure has been described based on the above exemplary embodiment and variations, it is needless to say that the present disclosure is not limited to the above embodiment and variations. The following is also included in the present disclosure.

(1) Specifically, each device described above may be achieved by a computer system which includes a microprocessor, a ROM, a RAM, a hard disk unit, a display unit, a keyboard, a mouse, and the like. A computer program is stored in the RAM or the hard disk unit. The operation of the microprocessor in accordance with the computer program allows each device to achieve its functionality. Here, the computer program includes a combination of instruction codes indicating instructions to a computer in order to achieve given functionality.

(2) Some or all of constituent elements included in each device described above may be included in a single system large scale integration (LSI: large scale integrated circuit). The system LSI is a super multi-function LSI manufactured by integrating multiple components into one chip, and is specifically a computer system configured so as to include a microprocessor, a ROM, a RAM, and so on. A computer program is stored in the RAM. The system LSI accomplishes its functions through the load of the computer program from the ROM to the RAM by the microprocessor and the operation of the microprocessor in accordance with the computer program.

(3) Some or all of constituent elements included in each device described above may be included in an IC card or a single module which can be attached to or detached from the device. The IC card or the module is a computer system which includes a microprocessor, a ROM, a RAM, and the like. The above super-multifunctional LSI may be included in the IC card or the module. The IC card or the module accomplishes its functions through the operation of the microprocessor in accordance with the computer program. This IC card or module may have tamper resistant properties.

(4) The present disclosure may be achieved by the methods described above. In addition, these methods may be achieved by a computer program implemented by a computer, or may be implemented by a digital signal which includes a computer program.

The present disclosure may be achieved by a computer program or a digital signal stored in a computer-readable recording medium such as, for example, a flexible disk, a hard disk, CD-ROM, MO, DVD, DVD-ROM, DVD-RAM, a blu-ray disc (BD), or a semiconductor memory. Alternatively, the present disclosure may be achieved by a digital signal stored in such a recording medium.

According to the present disclosure, the computer program or the digital signal may be transmitted via, for instance, data broadcasting or a network typified by electric telecommunication lines, wireless or wired communication lines, and the Internet.

The present disclosure may be a computer system which includes a microprocessor and a memory, the memory may have stored therein a computer program, and the microprocessor may operate in accordance with the computer program.

Another independent computer system may implement a program or a digital signal transported being stored in a recording medium, or a program or a digital signal transported via a network or the like.

(5) The above embodiment and variations may be combined.

As described above, the present disclosure provides a grip sensor with less error, and is in particular useful as a grip sensor of a steering wheel of a vehicle, for instance.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

What is claimed is:

1. A grip sensor comprising:
   a plurality of capacitive detectors which are disposed in a grip of a steering wheel of a vehicle, and output values which vary according to whether a human body is in contact; and
   a controller which determines, at a preset timing, a single reference value to be subtracted from each of the output values from the plurality of capacitive detectors, to determine whether the human body is in contact,
   wherein the controller identifies, from among the output values from the plurality of capacitive detectors at the preset timing, one or more first values each having an absolute value smaller than a first threshold, and one or more second values having an absolute value greater than or equal to the first threshold in response to a human body being in contact with the grip at a portion in which one or more of the plurality of capacitive detectors which has output the one or more second values is disposed, and
   the controller determines, as the single reference value, one of the one or more first values identified or an average of the one or more first values identified, and the controller excludes the one or more second values from being used as the single reference value.

2. The grip sensor according to claim 1, wherein the controller determines a previous reference value as the single reference value if all of the output values from the plurality of capacitive detectors at the preset timing have absolute values greater than or equal to the first threshold.

3. The grip sensor according to claim 1, wherein if the output values from the plurality of capacitive detectors at the preset timing include a value having an absolute value greater than or equal to a second threshold which is greater than the first threshold, the controller adjusts, based on magnitude of the value, a sensitivity of one of the plurality of capacitive detectors which has output the value.

4. The grip sensor according to claim 1, wherein if the single reference value is between the first threshold and a minimum reference value, the controller re-determines the single reference value based on a previous reference value and the single reference value, the minimum reference value having an absolute value smaller than the first threshold.

5. The grip sensor according to claim 1, wherein the preset timing includes at least one of times when the controller detects: operation of an ignition switch of the vehicle; operation of a shift lever; operation of a switch on an instrument panel of a driver seat; operation of a switch of a driver door; a driver being seated in the driver seat; and the driver wearing a seat belt.

6. The grip sensor according to claim 1, wherein the plurality of capacitive detectors include three or more capacitive detectors, and the controller corrects the single reference value for the plurality of capacitive detectors at preset time intervals.

7. The grip sensor according to claim 1, wherein the controller updates a previous reference value to be the single reference value in response to determining the single reference value.

8. The grip sensor according to claim 7, wherein, when determining a next reference value at a next preset timing, the controller determines the single reference value as the next reference value if all of the output values output from the plurality of capacitive detectors at the next preset timing have absolute values greater than or equal to the first threshold.

9. The grip sensor according to claim 1, wherein a number of the plurality of capacitive detectors is three for lowering a possibility that all of the plurality of capacitive detectors are contacted at the preset timing.

10. The grip sensor according to claim 1, wherein the controller determines, as the single reference value, the average of the one or more first values identified.

11. The grip sensor according to claim 1, wherein the controller determines, as the single reference value, the one of the one or more first values identified.

12. The grip sensor according to claim 11, wherein the one of the one or more first values identified is a smallest one of the one or more first values identified.

13. The grip sensor according to claim 1, wherein the preset timing includes all of times when the controller detects: operation of an ignition switch of the vehicle; operation of a shift lever; operation of a switch on an instrument panel of a driver seat; and operation of a switch of a driver door.

14. The grip sensor according to claim 1, wherein, when one of the output values from the plurality of capacitive detectors is greater than or equal to a second threshold, the controller adjusts a sensitivity of one of the plurality of capacitive detectors which has output the one of the output values.

15. The grip sensor according to claim 14, wherein, when the one of the output values from the plurality of capacitive detectors is greater than or equal to the second threshold, the controller adjusts the sensitivity of the one of the plurality of capacitive detectors which has output the one of the output values to the extent that the one of the output values is less than the second threshold.

16. The grip sensor according to claim 1, wherein, when one of the output values from the plurality of capacitive detectors is less than a second threshold, the controller adjusts a sensitivity of one of the plurality of capacitive detectors which has output the one of the output values.

17. The grip sensor according to claim 16, wherein, when the one of the output values from the plurality of capacitive detectors is less than the second threshold, the controller adjusts the sensitivity of the one of the plurality of capacitive detectors which has output the one of the output values to the extent that the one of the output values is not less than the second threshold.

18. The grip sensor according to claim 1, wherein, when the single reference value is between the first threshold and a second threshold, the controller re-determines the single reference value.

19. The grip sensor according to claim 1, wherein a number of the plurality of capacitive detectors is two, and each of the plurality of capacitive detectors is disposed along substantially half of the grip.

20. The grip sensor according to claim 1, wherein the plurality of capacitive detectors do not overlap along the grip.

\* \* \* \* \*